United States Patent
Maehara et al.

(10) Patent No.: US 6,737,264 B1
(45) Date of Patent: May 18, 2004

(54) METHOD FOR PURIFYING AND ISOLATING (2S,3S)- OR (2R,3S)-HALOHYDRIN DERIVATIVES

(75) Inventors: Katsuji Maehara, Hyogo (JP); Shigeru Kawano, Osaka (JP); Makoto Yamaguchi, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/869,297

(22) PCT Filed: Jan. 21, 2000

(86) PCT No.: PCT/JP00/00275

§ 371 (c)(1),
(2), (4) Date: Nov. 2, 2001

(87) PCT Pub. No.: WO00/43357

PCT Pub. Date: Jul. 27, 2000

(30) Foreign Application Priority Data

Jan. 21, 1999  (JP) ............................. 11/013033

(51) Int. Cl.$^7$ ................................. C12P 41/00
(52) U.S. Cl. ...................................... 435/280
(58) Field of Search .......................... 435/280

(56) References Cited

FOREIGN PATENT DOCUMENTS

EP           0691345 A2     1/1996

OTHER PUBLICATIONS

"A Practical Method for the Preparation of α'–Chloroketones of N–Carbamate Protected–α–Aminoacids", Chen et al; Tetrahedron Letters (vol. 38, No. 18) pp 3175–3178 (1997).

Stereoselective Synthesis of Erythro α–Amino Epoxides; Rotella, David P.; Tetrahedron Letters (vol. 36, No. 31) pp5453–5456 (1995).

*Primary Examiner*—Sandra E. Saucier
(74) *Attorney, Agent, or Firm*—Armstrong, Kratz, Quintos, Hanson & Brooks, LLP

(57) ABSTRACT

The present invention has for its object to provide a practical method for the purification and isolation on a commercial scale of said compound (1) or compound (2) in good yield and with high quality.

The present invention provides a purification/isolation method of a (2S,3S)-1-halo-2-hydroxy-3-N-(tert-butoxycarbonyl)amino-4-phenylbutane (1) or a (2R,3S)-1-halo-2-hydroxy-3-N-(tert-butoxycarbonyl)amino-4-phenylbutane (2) which comprises, for the purpose of removing contaminant impurity from a mixture containing at least one of said compounds (1) and (2), causing the objective compound (1) or compound (2) to be crystallized in the presence of a solvent comprised of a hydrocarbon solvent and then collecting the obtained crystals.

22 Claims, No Drawings

METHOD FOR PURIFYING AND ISOLATING (2S,3S)- OR (2R,3S)-HALOHYDRIN DERIVATIVES

TECHNICAL FIELD

The present invention relates to a method for purification and isolation of (2S,3S)-1-halo-2-hydroxy-3-N-(tert-butoxycarbonyl)amino-4-phenylbutanes of the general formula (1):

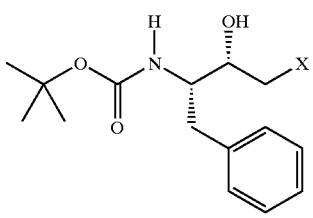

(1)

(wherein X represents a halogen atom) or (2R,3S)-1-halo-2-hydroxy-3-N-(tert-butoxycarbonyl)amino-4-phenylbutanes of the general formula (2):

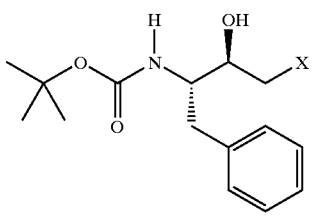

(2)

(wherein X represents a halogen atom). The above compounds are of great use as production intermediates of medicines, particularly HIV protease inhibitors [e.g. JP 06206857A, JP 08109131A and JP 08225557A].

BACKGROUND ART (2S,3S)-1-Halo-2-hydroxy-3-N-(tert-butoxycarbonyl) amino-4-phenylbutanes (1) [hereinafter referred to sometimes as compound (1)] and (2R,3S)-1-halo-2-hydroxy-3-N-(tert-butoxycarbonyl)amino-4-phenylbutanes (2) [hereinafter referred to sometimes as compound (2)] can be respectively produced by diastereo-selective reduction of the oxo group in position-2 of (3S)-1-halo-2-oxo-3-N-(tert-butoxycarbonyl)amino-4-phenylbutanes of the general formula (3) [hereinafter referred to sometimes as compound (3)]:

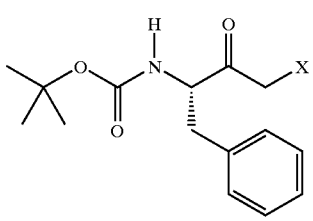

(3)

(wherein X represents a halogen atom) using a borane compound or an aluminum compound as a reducing agent (e.g. JP C6206857A, JP 08109131A and JP 08225557A) or by means of a strain of microorganism (e.g. JP 09000285A).

The compound (1) or compound (2) thus obtained usually contains the counterpart diastereomer compound (2) or compound (1) as a byproduct and the unreacted substrate compound (3) as impurity depending on reduction selectivity and conversion rate. Furthermore, the above compound (1) and compound (2) are not sufficiently stable and, therefore, in the course of process leading to final isolation, the loss of yield due to decomposition and the contamination with decomposition products tend to take place depending on conditions. The decomposition products, which are of several kinds, have not been fully identified as yet but at least (2S,3S)-1,2-epoxy-3-N-(tert-butoxycarbonyl)amino-4-phenylbutane of the following general formula (4):

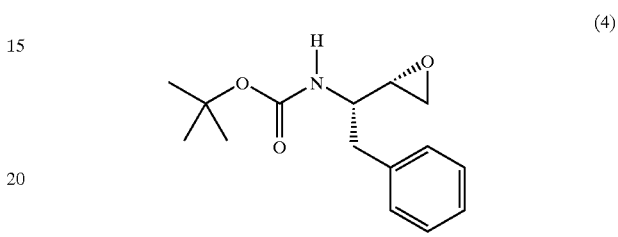

(4)

[(hereinafter referred to sometimes as compound (4)] and (2R,3S)-1,2-epoxy-3-N-(tert-butoxycarbonyl)amino-4-phenylbutane of the following general formula (5):

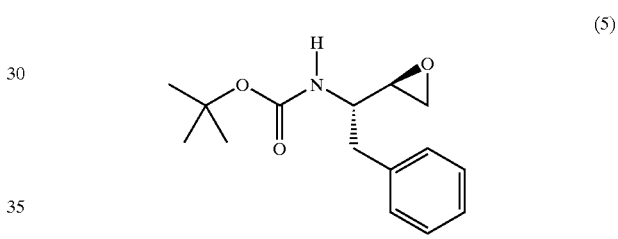

(5)

are known.

Therefore, in order that said compound (1) or compound (2) may be isolated in good yield and with high quality, it is necessary to use a sophisticated purification/isolation procedure insuring a minimum of contamination with said diastereomer compound (2) or (1), said unreacted substrate compound (3), said decomposition product compounds (4) and (5) and other structurally analogous contaminants.

For the purification and isolation of said compound (1), the following methods, among others, are known.

i) After the reduction reaction, the reaction mixture is quenched with $KHSO_4/H_2O$ and concentrated to give a yellow solid and this yellow solid is re-slurried with water, washed with hexane, and dried. Then, this dry solid is extracted with hot ethyl acetate and the extract is filtered after treatment with activated carbon and Celite, concentrated, and cooled to give lichenoid brown crystals. Yield 45.5%. (2S,3S) compound/(2R,3S) compound=95.6/2.0 (JP 08225557A).

ii) After the reduction reaction, the reaction mixture is quenched with $KHSO_4/H_2O$, extracted with ethyl acetate, dried over $MgSO_4$, filtered, and concentrated to give a white solid. This solid is recrystallized from hot ethyl acetate. Yield 50%. (2R,3S) compound content: a few % (JP 06206857A).

iii) After the reduction reaction, the reaction mixture is quenched with $KHSO_4/H_2O$, extracted with ethyl acetate, dried over $MgSO_4$, filtered and concentrated to give a grayish white solid. This solid is crystallized from hot ethyl acetate/hexane (50/50) to give needle-like crystals. Yield 53% (JP 08225557A).

For the isolation of said compound (2), the method for isolation by column chromatography, for instance, is known (JP 06206857A). However, there is not known a method for isolating crystals by crystallization procedure only.

Moreover, in these methods, the quality and yield of the product compound cannot necessarily be reconciled. Further, these conventional methods require the use of various reagents unsuitable for commercial-scale operation in substantial amounts and/or involve a concentration—crystallization—filtration procedure which is either time-consuming or complicated, so that none of the methods are fully satisfactory in operability or productivity. In other words, none of the known methods have proved satisfactory for practical mass production.

Under the circumstances, it has a great significance to establish a practical method for the purification/isolation on a mass-production scale of (2S,3S)-1-halo-2-hydroxy-3-N-(tert-butoxycarbonyl)amino-4-phenylbutanes (1) or (2R,3S)-1-halo-2-hydroxy-3-N-(tert-butoxycarbonyl)amino-4-phenylbutanes (2), which are useful production intermediates of HIV protease inhibitors.

SUMMARY OF THE INVENTION

In the above state of the art, the present invention has for its object to provide a practical method for the purification and isolation on a commercial scale of said compound (1) or compound (2) in good yield and with high quality.

The present invention, therefore, is concerned with a purification/isolation method of a (2S,3S)-1-halo-2-hydroxy-3-N-(tert-butoxycarbonyl)amino-4-phenylbutane of the following general formula (1):

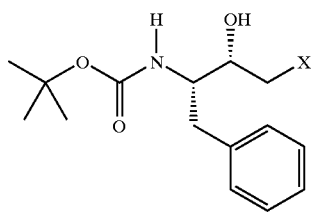

(1)

(wherein X represents a halogen atom) or a (2R,3S)-1-halo-2-hydroxy-3-N-(tert-butoxycarbonyl)amino-4-phenylbutane of the following general formula (2):

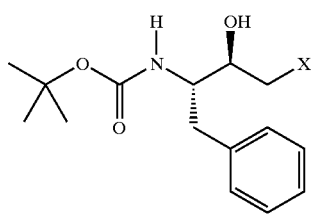

(2)

(wherein X represents a halogen atom)
which comprises, for the purpose of removing contaminant impurity from a mixture containing at least one of said (2S,3S)-1-halo-2-hydroxy-3-N-(tert-butoxycarbonyl)amino-4-phenylbutane (1) and (2R,3S)-1-halo-2-hydroxy-3-N-(tert-butoxycarbonyl)amino-4-phenylbutane (2), causing the objective compound (1) or compound (2) to be crystallized in the presence of a solvent comprised of a hydrocarbon solvent
and collecting the obtained crystals.

DISCLOSURE OF THE INVENTION

The purification/isolation method of the present invention comprises, for the purpose of removing contaminant impurity from a mixture containing at least one of said compound (1) and compound (2), causing the objective compound (1) or compound (2) to be crystallized in the presence of a solvent comprised of a hydrocarbon solvent and collecting the obtained crystals.

In the above general formulas (1), (2) and (3), X represents a halogen atom. The halogen atom includes fluorine, chlorine, bromine and iodine, although a chlorine atom or a bromine atom is preferred in terms of the ease of synthesis. The most preferred is a chlorine atom.

The mixture containing at least one of said compound (1) and compound (2) for use in the present invention can be obtained by, for example, the diastereo-selective reduction of a (3S)-1-halo-2-oxo-3-N-(tert-butoxycarbonyl)amino-4-phenylbutane of the above general formula (3) by means of a reducing agent, such as a borane compound and an aluminum compound, or by means of a strain of microorganism. Specifically, any of the known techniques can be liberally used (e.g. JP 06206857A, JP 08109131A, JP 08225557A and JP 09000285A).

The reducing agent for use in the above reduction reaction is not particularly restricted but includes sodium bis(2-methoxyethoxy)aluminum hydride, lithium aluminum hydride, sodium borohydride, potassium borohydride, tetramethylammonium borohydride; aluminum trialkoxides such as aluminum triisopropoxide and aluminum tri-sec-butoxide; lithium aluminum trialkoxyhydrides such as lithium aluminum tri-tert-butoxyhydride; substituted aluminum alkoxides such as methanesulfonyloxyaluminum diisopropoxide and ethanesulfonyloxyaluminum diisopropoxide; among others [e.g. JP 06206857A, JP 08109131A, JP 08225557A, JP 08099959, Japanese Patent Application H-9-162005, etc.]. These reducing agents are generally effective in preferentially producing said compound (1).

The microorganism for use in the above reduction reaction includes microorganisms belonging to any of the genera Candida, Geotrichum, Metchnikowia, Pachysolen, Pichia, Ogataea, Rhodotorula, Trichosporon, Zygosaccharomyces, Botryoascus, Cryptococcus, Citeromyces, Debaryomyces, Williopsis, Kloeckera, Lipomyces, Rhodosporidium, Rhodotorula, Saccharomycopsis and Wingea, among others. Generally, microorganisms belonging to the genus Candida, Geotrichum, Metchnikowia, Pachysolen, Pichia, Rhodotorula, Trichosporon or Botryoascus are effective in preferential production of said compound (1) and microorganisms belonging to the genus Candida, Pichia, Ogataea, Cryptococcus, Citeromyces, Debaryomyces, Williopsis, Kloeckera, Lipomyces, Rhodosporidium, Rhodotorula, Saccharomycopsis or Wingea are effective in preferential production of said compound (2) (cf. JP 09000285A).

The above compound (1) and/or compound (2) available on diastereo-selective reduction of said compound (3) is generally extracted into an organic phase in the presence of an organic solvent and water and the organic phase separated from the aqueous phase is optionally adjusted to a suitable concentration to give a mixture containing said compound (1) and/or compound (2) with advantage. Then, by causing the objective compound (1) or compound (2) to be crystallized from this mixture in the presence of a solvent comprised of a hydrocarbon solvent, said compound (1) and/or compound (2) can be expediently obtained in crystalline form without resort to a complicated procedure (e.g. concentration to dryness and isolation as a solid).

The above extraction is preferably carried out in the range of acidic to weakly basic. Under strongly basic conditions, the decomposition of said compound (4) or compound (5) is prominent to detract from the yield and quality of the crystal. The acidic to weakly basic range mentioned above generally corresponds to pH 0 to 9, preferably pH 1 to 8.

An acid and/or a base can be used to establish such acidic to weakly basic conditions. The acid or base for use is not particularly restricted. However, the acid is preferably a mineral acid, such as hydrochloric acid and sulfuric acid. The base is preferably an alkali metal hydroxide, such as sodium hydroxide and potassium hydroxide; an alkali metal carbonate such as sodium carbonate and potassium carbonate; or an alkali metal hydrogen carbonate such as sodium hydrogen carbonate and potassium hydrogen carbonate.

The organic solvent for use in said extraction is not particularly restricted but in consideration of the subsequent crystallization procedure, use of a hydrocarbon solvent is preferred. Especially when the compound to be obtained is compound (1), it is more preferred to use an aromatic hydrocarbon solvent. When the compound (2) is to be obtained, use of an aromatic hydrocarbon solvent and/or an aliphatic hydrocarbon solvent is preferred. As said hydrocarbon solvent, aromatic hydrocarbon solvent and aliphatic hydrocarbon solvent, the specific solvents to be mentioned hereinafter can be used with advantage.

The organic solvent for said extraction, which is preferred in consideration of the subsequent removal of water from the separated organic phase, includes:

an organic solvent which is not miscible with water but forms an azeotropic mixture with water, the water content of which azeotropic mixture is about 1/10 volume part to about 1/2 volume part, an organic solvent which is immiscible with water, i.e. the solubility of water therein at the temperature of contact with an aqueous phase is not more than 1/100 weight part, and is capable of forming an azeotropic mixture with water, or a solvent mixture containing at least one of the organic solvents defined above.

As the preferred organic solvents of the former category, there can be mentioned aromatic hydrocarbon solvents such as benzene, toluene, xylene, ethylbenzene, etc.; ketone solvents such as 2-pentanone, methyl isobutyl ketone, etc.; and acetic acid esters such as propyl acetate, butyl acetate, etc., among others. As the preferred organic solvents of the latter category, there can be mentioned aromatic hydrocarbon solvents such as benzene, toluene, xylene, ethylbenzene, etc.; and halogenated hydrocarbon solvents such as methylene chloride, chloroform, etc., among others. However, in terms of extraction efficiency, elimination of water from the separated organic phase, and utility as a crystallization solvent, an aromatic hydrocarbon solvent such as benzene, toluene, xylene and ethylbenzene is preferred and, among these, toluene or xylene is more preferred, with toluene being the most desirable.

The organic phase obtained by such extraction may be washed with water, where necessary, under acidic to weakly basic conditions. The water which can be used for this purpose is not particularly restricted; thus, it includes not only water as such but also aqueous hydrochloric acid or sulfuric acid and aqueous solutions of sodium hydrogen carbonate, sodium hydroxide, sodium chloride and sodium sulfate, among others.

The resulting organic phase containing said compound (1) and/or compound (2) is concentrated (preferably dehydrated by azeotropic distillation) to a concentration suitable for crystallization.

The mixture containing said compound (1) and/or compound (2) may be prepared, as described above, by extracting the diastereo-selective reduction product of said compound (3) with a suitable organic solvent and substituting said hydrocarbon solvent for the solvent of the separated organic phase but may also be prepared by extracting said reduction product with said hydrocarbon solvent and directly concentrating the organic extract.

Particularly for obtaining a mixture predominantly containing said compound (1), the recommended procedure comprises producing said compound (1) dominantly by said reduction reaction, extracting the reaction mixture with an aromatic hydrocarbon solvent and concentrating the separated organic phase.

On the other hand, the recommended procedure for obtaining a mixture predominantly containing said compound (2) comprises carrying out said reduction reaction preferentially giving rise to said compound (2), extracting the reaction mixture with an organic solvent, and finally substituting an aliphatic hydrocarbon solvent for the solvent of the separated organic phase. More preferred procedure comprises extracting said reduction mixture with an aromatic hydrocarbon solvent and substituting an aliphatic hydrocarbon solvent for the solvent of the separated organic phase.

Since said compound (1) and compound (2) are not necessarily thermally stable, the concentration (azeotropic dehydration) procedure is preferably carried through quickly.

For minimizing the decomposition, the procedure for giving said mixture is carried out preferably at a temperature not exceeding 60° C., more preferably not higher than 50° C.

The purification/isolation method of the present invention comprises causing either compound (1) or compound (2) to be crystallized from the above mixture, in which it occurs predominantly, in the presence of a solvent comprised of a hydrocarbon solvent and collecting the resulting crystal and, at the same time, removing the impurity in said mixture into the mother liquor comprised of said hydrocarbon solvent.

The hydrocarbon solvent mentioned above is not particularly restricted but includes aromatic hydrocarbon solvents such as benzene, toluene, xylene, ethylbenzene, etc.; and aliphatic hydrocarbon solvents such as pentane, hexane, methylcyclohexane, heptane and so on. The aromatic hydrocarbon solvents are preferably those containing 6 to 8 carbon atoms, more preferably toluene, xylene and ethylbenzene, with toluene being particularly preferred. The aliphatic hydrocarbon solvents are preferably those containing 5 to 7 carbon atoms and more preferably hexane, methylcyclohexane and heptane, with hexane being particularly preferred. The hydrocarbon solvents mentioned above may be used each independently or, where necessary, may be used as a mixture of two or more species. The solvent comprised of such hydrocarbon solvent may contain other kinds of solvents within the range not adversely affecting the result. As such other kinds of solvents, the organic solvents mentioned hereinbefore can be employed.

Particularly when said compound (2) is to be collected, the presence of said aliphatic hydrocarbon solvent is instrumental for effective crystallization of the compound (2).

The hydrocarbon solvents mentioned above may be used each independently but may optionally be used in a suitable combination. Thus, in the crystallization of said compound (1), the procedure is carried out in such a manner that said aromatic hydrocarbon solvent will be a dominant solvent at completion of crystallization and, if necessary, an aliphatic hydrocarbon solvent maybe used as an auxiliary solvent. On the other hand, for crystallization of said compound (2), the procedure is carried out in such a manner that said aliphatic hydrocarbon solvent will be a dominant solvent at completion of crystallization and, if necessary, an aromatic hydrocarbon solvent may be used as an auxiliary solvent.

The term " . . . will be a dominant solvent" means that the particular solvent accounts for the largest proportion of the solvent used, generally accounting for not less than ½ by volume. Particularly, the proportion of said aliphatic hydrocarbon solvent for the crystallization of compound (2) at crystallization is preferably not less than ½ by volume, more preferably not less than ⅔ by volume, still more preferably not less than ¾ by volume, and the proportion mentioned above is preferably achieved by sequential addition of the aliphatic hydrocarbon solvent.

On the other hand, the term " . . . used concomitantly as an auxiliary solvent" means that the particular solvent accounts for a lesser proportion as compared with said dominant solvent, generally accounting for less than ½ of the total volume of the solvent.

In accordance with the purification/isolation method of the invention, said compound (1) and compound (2) can be fractionated, for example from a mixture containing said compound (1) and compound (2), in which the former compound (1) is predominant, by causing said compound (1) to be crystallized in the presence of said aromatic hydrocarbon solvent as the dominant solvent, collecting crystals of said compound (1) in a high yield, then substituting said aliphatic hydrocarbon solvent for the dominant solvent of the mother liquor predominantly having the residual compound (2) and causing the compound (2) to be crystallized and collecting the crystals. In the stage where the compound (2) is crystallized, an aromatic hydrocarbon solvent can be utilized as an auxiliary solvent and, preferably, seed crystals can be added for promoting the crystallization of compound (2).

In the method of the present invention, the crystallization can be carried out by the known procedure, for example crystallization by cooling or by concentration.

The crystallization temperature in the method of the invention is preferably not higher than 60° C., more preferably not over 50° C. For an improved yield, cooling is preferably carried out where appropriate (crystallization by cooling).

Where necessary, seed crystals may be added for promoting crystallization.

The crystals of compound (1) or compound (2) thus formed can be separated from the mother liquor by a known solid-liquid separation technique, such as suction filtration, pressure filtration or centrifugation and the wet product obtained can be washed with the same solvent as the solvent used for crystallization and, where necessary, dried in vacuo to give a dry product.

The whole of the above procedure for isolating compound (1) or (2) as crystals is preferably carried out at a temperature not exceeding 60° C., more preferably not over 50° C., so as to minimize decomposition of the object compound.

In accordance with the purification/isolation method of the invention described above, the compound (1) or compound (2) can be obtained by a single crystallization procedure, in a very high yield, more efficiently than in the prior art, and very satisfactorily (in terms of quality, filterability, etc.). Of course, this purification/isolation method can be utilized as a recrystallization method as well.

The principal impurity compounds which tend to contaminate the mixture predominantly containing said compound (1) and are removed by the purification/isolation method of the invention are (2R,3S)-1-halo-2-hydroxy-3-N-(tert-butoxycarbonyl)amino-4-phenylbutane of said general formula (2), (3S)-1-halo-2-oxo-3-N-(tert-butoxycarbonyl) amino-4-phenylbutane of said general formula (3), (2S,3S)-1,2-epoxy-3-N-(tert-butoxycarbonyl)amino-4-phenylbutane of said is general formula (4) and/or (2R,3S)-1,2-epoxy-3-N-(tert-butoxycarbonyl)amino-4-phenylbutane of said general formula (5).

The principal impurity compounds which tend to contaminate the mixture predominantly containing said compound (2) and are removed by the purification/isolation method of the invention are (2S,3S)-1-halo-2-hydroxy-3-N-(tert-butoxycarbonyl)amino-4-phenylbutane of said general formula (1), (3S)-1-halo-2-oxo-3-N-(tert-butoxycarbonyl) amino-4-phenylbutane of said general formula (3), (2S,3S)-1,2-epoxy-3-N-(tert-butoxycarbonyl)amino-4-phenylbutane of said general formula (4), and/or (2R,33)-1,2-epoxy-3-N-(tert-butoxycarbonyl)amino-4-phenylbutane of said general formula (5).

BEST MODE FOR CARRYING OUT THE INVENTION

The following examples illustrate the present invention in further detail, it being to be understood that the scope of the invention is by no means defined by these examples.

EXAMPLE 1

A solution containing 4.6 g of (2S,3S)-1-chloro-2-hydroxy-3-N-(tert-butoxycarbonyl)amino-4-phenylbutane in ethyl acetate-toluene [toluene/ethyl acetate=3:1 (v/v)] was concentrated from 101.7 g to 42.0 g under reduced pressure (ca 100 mmHg) in a nitrogen atmosphere at an internal temperature of 30 to 40° C. with vigorous stirring. Then, with vigorous stirring continued, the solvent was substituted by distilling off while toluene was added at a rate necessary to maintain the liquid volume constant at an internal temperature of 5 to 50 mmHg until the ethyl acetate content had been reduced to 3 weight % [treatment concentration 10% (substrate weight/solution weight)]. The atmospheric pressure was reestablished with nitrogen gas and the mixture was held under nitrogen at 50° C. with vigorous stirring for 1 hour, then cooled gradually to an internal temperature of 5° C., and finally held at this internal temperature of 5° C. for 1 hour.

The crystals which had separated out were collected by suction filtration, drained thoroughly, and washed with 15 ml of toluene (filterability was excellent). This crystal was dried in vacuo (ca 1 to 10 mmHg, 20 to 40° C., ca 4 hours) to give 4.5 g (yield 97%) of (2S,3S)-1-chloro-2-hydroxy-3-N-(tert-butoxycarbonyl)amino-4-phenylbutane as crystals. The Quality of (2S,3S)-1-chloro-2-hydroxy-3-N-(tert-butoxycarbonyl)amino-4-phenylbutane Before Treatment (After Concentration to Dryness In Vacuo)
Purity: 82.3 weight %
(2S,3S) compound/((2S,3S) compound+(2R,3S) compound): 95.0%
(3S)-1-Chloro-2-oxo-3-N-(tert-butoxycarbonyl)amino-4-phenylbutane content: 1.1 area %
The Quality of (2S,3S)-1-chloro-2-hydroxy-3-N-(tert-butoxycarbonyl)amino-4-phenylbutane Crystals After Treatment
Purity: 99.7 weight %
(2S,3S) compound/((2S,3S) compound)+(2R,3S) compound: 99.7%
(3S)-1-Chloro-2-oxo-3-N-(tert-butoxycarbonyl)amino-4-phenylbutane content: less than 0.1 area %

(2S,3S)-1,2-epoxy-3-N-(tert-butoxycarbonyl)amino-4-phenylbutane: less than 0.1 area %
(2R,3S)-1,2-epoxy-3-N-(tert-butoxycarbonyl)amino-4-phenylbutane: less than 0.1 area %
Mean crystal grain diameter: ca 300 to 400 μm

EXAMPLE 2

A solution containing 2.7 g of (2R,3S)-1-chloro-2-hydroxy-3-N-(tert-butoxycarbonyl)amino-4-phenylbutane in toluene was concentrated from 15.6 g to 6.9 g under reduced pressure (ca 100 mmHg) in a nitrogen atmosphere at an internal temperature of 30 to 40° C. with vigorous stirring. With vigorous stirring continued, 18.1 g of hexane was added [treatment concentration: ca 11 wt % (substrate weight/solution weight)]. Then, with vigorous stirring continued, the mixture was held at 40° C. for 1 hour, then cooled gradually to an internal temperature of −5° C., and held at this internal temperature of −5° C. for 1 hour.

The crystals which had separated out were collected by suction-filtration, drained thoroughly, and washed with 10 ml of hexane (filterability was excellent). This crystal was dried in vacuo (ca 1 to 10 mmHg, 20 to 40° C., ca 3 hours) to give 2.6 g (yield 94.5%) of (2R,3S)-1-chloro-2-hydroxy-3-N-(tert-butoxycarbonyl)amino-4-phenylbutane as crystals.
The Quality of (2R,3S)-1-chloro-2-hydroxy-3-N-(tert-butoxycarbonyl)amino-4-phenylbutane Before Treatment (After Concentration to Dryness In Vacuo)
Purity: 96.8 weight %
(2R,3S) compound/((2R,3S) compound+(2S,3S) compound): 99.7%
(3S)-1-Chloro-2-oxo-3-N-(tert-butoxycarbonyl)amino-4-phenylbutane content: 1.4 area %
The Quality of (2R,3S)-1-chloro-2-hydroxy-3-N-(tert-butoxycarbonyl)amino-4-phenylbutane Crystals After Treatment
Purity: 99.9 weight %
(2R,3S) compound/((2R,3S) compound+(2S,3S) compound): not less than 99.9%
(3S)-1-Chloro-2-oxo-3-N-(tert-butoxycarbonyl)amino-4-phenylbutane content: less than 0.1 area %
(2S,3S)-1,2-epoxy-3-N-(tert-butoxycarbonyl)amino-4-phenylbutane: less than 0.1 area %
(2R,3S)-1,2-epoxy-3-N-(tert-butoxycarbonyl)amino-4-phenylbutane: less than 0.1 area %
Mean crystal grain diameter: not less than 425 μm

EXAMPLE 3

A solution containing 8.4 g of (2S,3S)-1-chloro-2-hydroxy-3-N-(tert-butoxycarbonyl)amino-4-phenylbutane and 2.5 g of (2R,3S)-1-chloro-2-hydroxy-3-N-(tert-butoxycarbonyl)amino-4-phenylbutane in toluene-ethyl acetate [toluene/ethyl acetate=3:1 (v/v)] was concentrated from 200.0 g to 83.8 g under reduced pressure (ca 100 mmHg) in a nitrogen atmosphere at an internal temperature of 30 to 40° C. with vigorous stirring. With vigorous stirring continued, the solvent was substituted by distilling off at an internal pressure of 5 to 50 mmHg while the liquid volume was maintained constant with toluene until the ethyl acetate content had been reduced to 4 weight % [treatment temperature ca 10% (substrate weight/solution weight)]. The atmospheric pressure was reestablished with nitrogen gas and the mixture was held under nitrogen at 50° C. with vigorous stirring for 1 hour, then cooled gradually to an internal temperature of 5° C., and finally held at this internal temperature of 5° C. for 1 hour.

The crystals which had separated out were collected by suction-filtration, drained thoroughly, and washed with 30 ml of toluene. The wet crystals thus obtained were dried in vacuo (ca 1 to 10 mmHg, 20 to 40° C., ca 10 hours) to give 8.4 g of (2S,3S)-1-chloro-2-hydroxy-3-N-(tert-butoxycarbonyl)amino-4-phenylbutane as crystals.

Then, while the mother liquor, 47.8 g, was held at an internal temperature of 30 to 40° C. in a nitrogen atmosphere, the solvent was concentrated under reduced pressure (ca 100 mmHg) with vigorous stirring until the liquid volume had been reduced to 5.4 g. Then, with vigorous stirring continued, 13.7 g of hexane was added [treatment concentration ca 11 wt. % (substrate weight/solution weight)] and the mixture was passed through a filter to give a pre-crystallization liquor containing 2.2 g of (2R,3S)-1-chloro-2-hydroxy-3-N-(tert-butoxycarbonyl)amino-4-phenylbutane.

Then, after 10 ml of hexane was added, 3 mg of crystals of (2R,3S)-1-chloro-2-hydroxy-3-N-(tert-butoxycarbonyl)amino-4-phenylbutane were added as seed crystals. The mixture was stirred at 20° C. for 12 hours, then cooled to 5° C., and held at that temperature for 1 hour to complete the crystallization procedure.

The crystals which had separated out were collected by suction-filtration, drained thoroughly, and washed with 10 ml of hexane. This crystal was dried in vacuo (ca 1 to 10 mmHg, 20 to 40° C., ca 3 hours) to give 1.2 g of (2R,3S)-1-chloro-2-hydroxy-3-N-(tert-butoxycarbonyl)amino-4-phenylbutane as crystals.
The Quality of the Pre-treatment Solution Containing (2S,3S)-1-chloro-2-hydroxy-3-N-(tert-butoxycarbonyl)amino-4-phenylbutane and (2R,3S)-1-chloro-2-hydroxy-3-N-(tert-butoxycarbonyl)amino-4-phenylbutane (After Concentration to Dryness In Vacuo)
(2S,3S) compound/((2S,3S) compound+(2R,3S) compound): 76.8%
The quality of (2S,3S)-1-chloro-2-hydroxy-3-N-(tert-butoxycarbonyl)amino-4-phenylbutane Crystals After Treatment
(2S,3S) compound/((2S,3S) compound+(2R,3S) compound): 97.8%
(2S,3S)-1,2-epoxy-3-N-(tert-butoxycarbonyl)amino-4-phenylbutane: less than 0.1 area %
(2R,3S)-1,2-epoxy-3-N-(tert-butoxycarbonyl)amino-4-phenylbutane: less than 0.1 area %
The Quality of the Solution Containing (2R,3S)-1-chloro-2-hydroxy-3-N-(tert-butoxycarbonyl)amino-4-phenylbutane Before Crystallization (After Concentration to Dryness In Vacuo)
(2R,3S) compound/((2R,3S) compound+(2S,3S) compound): 90.8%
The Quality of (2R,3S)-1-chloro-2-hydroxy-3-N-(tert-butoxycarbonyl)amino-4-phenylbutane Crystals After Treatment
(2R,3S) compound/((2R,3S) compound+(2S,3S) compound): 97.7%
(2S,3S)-1,2-epoxy-3-N-(tert-butoxycarbonyl)amino-4-phenylbutane: less than 0.1 area %
(2R,3S)-i,2-epoxy-3-N-(tert-butoxycarbonyl)amino-4-phenylbutane: less than 0.1 area %

Reference Example 1

Method for Synthesis of (2S,3S)-1-chloro-2-hydroxy-3-N-(tert-butoxycarbonyl)amino-4-phenylbutane From (3S)-1-chloro-2-oxo-3-N-(tert-butoxycarbonyl)amino-4-phenylbutane To 25.2 ml (25.7 mmol) of a solution of diisobutylaluminum hydride (1.02 M) in toluene was added 3.1 g of 2-propanol at room temperature, and the mixture was stirred at room temperature for 1 hour. To this was added 5.1 g (17.1 mmol) of (3S)-1-chloro-2-oxo-3-N-(tert-butoxycarbonyl) amino-4-phenylbutane. The mixture was stirred at room temperature for 2 hours, after which hydrolysis was carried out with 1 N-hydrochloric acid under ice-cooling. This reaction mixture was extracted with ethyl acetate, the aqueous layer was separated, and the organic layer was washed with water to give 101.7 g of a solution containing 4.6 g (yield 90%) of (2S,3S)-1-chloro-2-hydroxy-3-N-(tert-butoxycarbonyl)amino-4-phenylbutane.

The Quality of (2S,3S)-1-chloro-2-hydroxy-3-N-tert-butoxycarbonyl)amino-4-phenylbutane Thus Obtained (After Concentration to Dryness In Vacuo Purity: 82.3%
(2S,3S) compound/((2S,3S) compound+(2R,3S) compound): 95.0%
(3S)-1-Chloro-2-oxo-3-N-(tert-butoxycarbonyl)amino-4-phenylbutane content: 1.1 area %

Reference Example 2

Method for Synthesis of (2R,3S)-1-chloro-2-hydroxy-3-N-(tert-butoxycarbonyl)amino-4-phenylbutane From (3S)-1-chloro-2-oxo-3-N-(tert-butoxycarbonyl)amino-4-phenylbutane An large test tube was charged with 5 ml of a liquid medium (pH 7) composed of 40 g glucose, 3 g yeast extract, 6.5 g diammonium hydrogen phosphate, 1 g potassium dihydrogen phosphate, 0.8 g magnesium sulfate.7H$_2$O, 60 mg zinc sulfate.7H$_2$O, 90 mg iron sulfate.7H$_2$O, 5 mg copper sulfate.5H$_2$O, 10 mg manganese sulfate.4H$_2$O and 100 mg sodium chloride (all per liter), and steam-sterilized at 120° C. for 20 minutes. This liquid medium was aseptically inoculated with a loopful of *Debaryomyces robertslae* IFO 1277 and incubated under shaking at 30° C. for 48 hours.

A 500 ml-Sakaguchi flask was charged with 45 ml of a liquid medium composed of 3 g yeast extract, 6.5 g diammonium hydrogen phosphate, 1 g potassium dihydrogen phosphate, 0.8 g magnesium sulfate.7H$_2$O, 60 mg zinc sulfate.7H$_2$O, 90 mg iron sulfate.7H$_2$O, 5 mg copper sulfate.5H$_2$O, 10 mg manganese sulfate.4H$_2$O and 100 mg sodium chloride (all per 900 ml) and 1 drop of Adekanol, followed by sterilization. This flask was aseptically inoculated with 5 ml of sterilized 40% aqueous solution of glucose and 1 ml of the above culture and incubated under shaking at 30° C. for 24 hours to prepare a seed culture. A 5-L jar fermenter was charged with 2.25 L of the same liquid medium as above and 5 drops of Adekanol, sterilized, inoculated with 250 ml of sterilized 40% aqueous glucose solution and 50 ml of said seed culture, and incubated at a cultural temperature of 30° C. and an agitation speed of 600 rpm with 1.5 L/min aeration for 25 hours. When the culture system pH dropped below 5.5 during cultivation, the system was adjusted to pH 5.5 with 5 N-aqueous sodium hydroxide solution as needed.

A 5-L jar fermenter was charged with 2.5 L of the above culture, 23.7 g of (3S)-1-chloro-2-oxo-3-N-(tert-butoxycarbonyl)amino-4-phenylbutane and 100 g of glucose, a reduction reaction was carried out at 30° C. with stirring for 63 hours. The reaction mixture was maintained at pH 7 with 5 N-aqueous sodium hydroxide solution. Furthermore, glucose was added during the reaction where appropriate.

After completion of the reaction, the reaction mixture was extracted with 25 L of ethyl acetate and the organic layer was concentrated to dryness to give 24.0 g of a solid containing 23.3 g of (2R,3S)-1-chloro-2-hydroxy-3-N-(tert-butoxycarbonyl)amino-4-phenylbutane (yield 98%).

The Quality of the Solid Containing (2R,3S)-1-chloro-2-hydroxy-3-N-(tert-butoxycarbonyl)amino-4-phenylbutane Purity: 96.8 weight %
(2R,3S) compound/((2S,3S) compound+(2R,3S) compound): 99.7%
(3S)-1-Chloro-2-oxo-3-N-(tert-butoxycarbonyl)amino-4-phenylbutane content: 1.4 area %

INDUSTRIAL APPLICABILITY

The present invention, constituted as above, provides a purification/isolation technology which can be carried out expediently and efficiently on a commercial scale for providing a (2S,3S)-1-halo-2-hydroxy-3-N-(tert-butoxycarbonyl)amino-4-phenylbutane or a (2R,3S)-1-halo-2-hydroxy-3-N-(tert-butoxycarbonyl)amino-4-phenylbutane in good yield and with improved quality.

What is claimed is:

1. A purification/isolation method of a (2R,3S)-1-halo-2-hydroxy-3-N-(tert-butoxycarbonyl) amino-4-phenylbutane of the following formula (2):

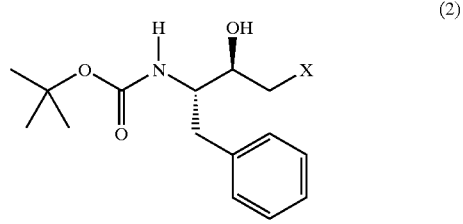

(2)

wherein X represents a halogen atom
which comprises, for the purpose of removing contaminant impurity from a mixture containing (2R,3S)-halo-2-hydroxy-3-N-(tert-butoxycarbonyl)amino-4-phenylbutane (2),
crystallizing the compound (2) in the presence of an aliphatic hydrocarbon solvent and collecting the obtained crystals.

2. The purification/isolation method according to claim 1 wherein an aromatic hydrocarbon solvent is used concomitantly as an auxiliary solvent.

3. The purification/isolation method according to claim 2 wherein the aliphatic hydrocarbon solvent accounts for not less than ½ of the total solvent volume at completion of crystallization.

4. The purification/isolation method according to claim 1, 2 or 3 which comprises crystallizing a compound (1) represented by the following formula (1):

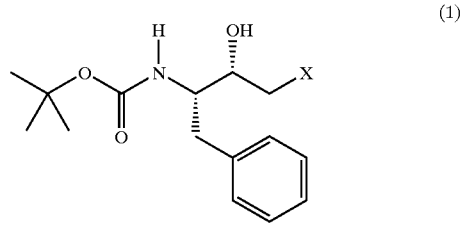

(1)

wherein X represents a halogen atom, from a mixture containing said compound (1) and compound (2) in the presence of an aromatic hydrocarbon solvent as the major solvent and collecting the crystals, and then crystallizing said compound (2) by substituting an aliphatic hydrocarbon solvent for the major solvent of the mother liquor predominantly having the residual compound (2)

and collecting the obtained crystals.

5. A purification/isolation method of a compound (1) and a compound (2)

which comprises crystallizing said compound (1) from a mixture containing the compound (1) and the compound (2) in the presence of an aromatic hydrocarbon solvent as the major solvent and collecting the crystals, and then crystallizing said compound (2) by substituting an aliphatic hydrocarbon solvent for the major solvent of the mother liquor predominantly having the residual compound (2).

6. The purification/isolation method according to claim 5 wherein an aliphatic hydrocarbon solvent is used concomitantly as an auxiliary solvent at crystallization of the compound (1).

7. The purification/isolation method according to claim 1, 2, 3, 5 or 6 wherein the crystallization is carried out at a temperature not exceeding 60° C.

8. The purification/isolation method according to claim 1, 2, 3, 5, or 6 wherein a mixture containing the compound (2) is obtained by diastereo-selective reduction of a (3S)-1-halo-2-oxo-3-N-(tert-butoxycarbonyl)amino-4-phenylbutane of the following formula (3):

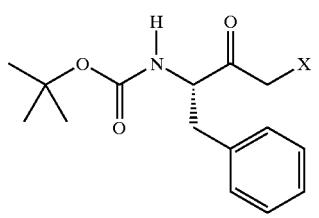

(3)

wherein X represents a halogen atom.

9. The purification/isolation method according to claim 8 wherein the diastereo-selective reduction is carried out either by using a sodium bis(2-methoxy-ethoxy) aluminum hydride, lithium aluminum hydride, sodium borohydride, potassium borohydride, tetramethylammonium borohydride, an aluminum trialkoxide, a lithium aluminum trialkoxy halide or a substituted aluminum alkoxide as a reducing agent or by using a strain of microorganism belonging to the genus Candida, Geotrichum, Metchnikowia, Pachysolen, Pichia, Rhodotorula, Trichosporon, or Botryoascus.

10. The purification/isolation method according to claim 8 wherein the diastereo-selective reduction is carried out either by using a stain of microorganism belonging to the genus Candida, Pichia, Ogataea, Cryptococcus, Citeromyces, Debaryomyces, Williopsis, Kloeckera, Lipomyces, Rhodosporidium, Rhodotorula, Saccharomycopsis or Wingea.

11. The purification/isolation method according to claim 8 wherein the mixture containing the compound (2) is obtained by subjecting the compound (3) to diastereo-selective reduction, extracting said compound (2) form the resulting reaction mixture into an organic phase in the presence of an organic solvent and water, separating said organic phase from the aqueous phase and adjusting it to a concentration suitable for crystallization.

12. The purification/isolation method according to claim 11 wherein the mixture containing the compound (2) is obtained by subjecting compound (3) to diastereo-selective reduction, extracting the reaction mixture with a hydrocarbon solvent and concentrating the separated organic phase or extracting the reaction mixture with an organic solvent and finally substituting a hydrocarbon solvent for the solvent of the separated organic phase.

13. The purification/isolation method according to claim 12 wherein the mixture containing the compound (2) is obtained by subjecting said compound (3) to reduction, extracting the reaction mixture with an organic solvent and finally substituting an aliphatic hydrocarbon solvent for the solvent of the separated organic phase.

14. The purification/isolation method according to claim 13 wherein the mixture containing the compound (2) is obtained by subjecting said compound (3) to reduction, extracting the reaction mixture with an aromatic organic solvent and finally substituting an aliphatic hydrocarbon solvent for the solvent of the separated organic phase.

15. The purification/isolation method according to claim 11 wherein the procedure for obtaining the mixture containing the compound (2) is carried out at a temperature not exceeding 60° C.

16. The purification/isolation method according to claim 1, 2, 3, 5 or 6 wherein the whole procedure for obtaining the compound (2) as crystals is carried out at a temperature not exceeding 60° C.

17. The purification/isolation method according to claim 4 or 5 wherein the aromatic hydrocarbon solvent is at least one member selected from the group consisting of benzene, toluene, xylene, and ethylbenzene.

18. The purification/isolation method according to claim 17 wherein the aromatic hydrocarbon solvent is toluene.

19. The purification/isolation method according to claim 1, 2, 3, 5 or 6 wherein the aliphatic hydrocarbon solvent is at least one member selected from the group consisting of pentane, hexane, methylcyclohexane and heptane.

20. The purification/isolation method according to claim 19 wherein the aliphatic hydrocarbon solvent is hexane.

21. The purification/isolation method according to claim 1, 2, 3, 5, or 6 wherein the impurity contaminating the mixture containing the compound (2) is at least one member selected from the group consisting of said compound (1), which is the diastereomer, the compound (3), (2S,3S)-1,2-epoxy-3-N-(tert-butoxycarbonyl)amino-4-phenylbutane of the following formula (4):

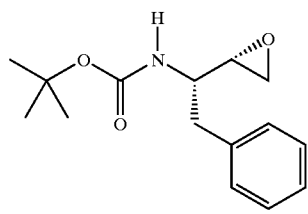
(4)
and (2R,3S)-1,2-epoxy-3-N-(tert-butoxycarbonyl)amino-4-phenylbutane of the following general formula (5):
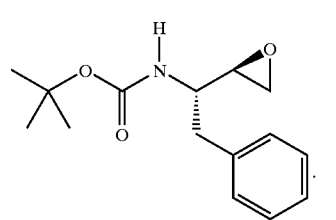
(5)
22. The purification/isolation method according to claim 1, 2, 3, 5 or 6
wherein the halogen atom represented by X in the formula (1), the formula (2) and the formula (3) is chlorine.
* * * * *